(12) United States Patent
Lin et al.

(10) Patent No.: US 11,739,088 B2
(45) Date of Patent: Aug. 29, 2023

(54) SYNTHESIS OF HETEROCYCLIC COMPOUNDS

(71) Applicant: Plexxikon Inc., Berkeley, CA (US)

(72) Inventors: Jack Lin, Hercules, CA (US); Jason Walters, Union City, CA (US)

(73) Assignee: PLEXXIKON INC., Basking Ridge, NJ (US)

( * ) Notice: Subject to any disclaimer, the term of this patent is extended or adjusted under 35 U.S.C. 154(b) by 19 days.

(21) Appl. No.: 17/243,358

(22) Filed: Apr. 28, 2021

(65) Prior Publication Data

US 2021/0340139 A1    Nov. 4, 2021

Related U.S. Application Data

(60) Provisional application No. 63/017,587, filed on Apr. 29, 2020.

(51) Int. Cl.
*C07D 213/76*   (2006.01)
*C07D 471/04*   (2006.01)

(52) U.S. Cl.
CPC ......... *C07D 471/04* (2013.01); *C07D 213/76* (2013.01)

(58) Field of Classification Search
CPC .................................................. C07D 213/76
See application file for complete search history.

(56) References Cited

FOREIGN PATENT DOCUMENTS

| WO | 2014/100620 A2 | 6/2014 | |
| WO | WO-2014100620 A2 * | 6/2014 | ........... A61K 31/437 |

OTHER PUBLICATIONS

American Chemical Service. Chemical Abstract Service. RN 2509931-12-6. Entered into STN: Nov. 11, 2020. (Year: 2020).*
Majumdar et al., "Regioselective synthesis of substituted pyrrolopyridines based on Pd(II)-mediated cross coupling and base induced heteroannulation", Tetrahedron Lett. 2007, vol. 48, No. 39, pp. 6951-6953.
Database Registry Service, Columbus, Ohio, US, "N-[5-nitro-3-(2-phenylethynyl)-2-pyridinyl]-acetamide", Aurora Fine Chemicals, Dec. 9, 2020, retrieved from STN, Database Accession No. 2552389-78-1, Abstract.
Database Registry Service, Columbus, Ohio, US, "N-[3-[2-(1-methyl-1H-pyrazole-3-yl)ethynyl]-5-nitro-2-pyridinyl]-acetamide", Aurora Fine Chemicals, Nov. 11, 2020, retrieved from STN, Database Accession No. 2509931-12-6, Abstract.
International Search Report and Written Opinion of the International Searching Authority mailed in International Application No. PCT/US2021/029699 dated Jul. 12, 2021.

* cited by examiner

*Primary Examiner* — John S Kenyon
(74) *Attorney, Agent, or Firm* — McDermott Will & Emery LLP

(57) ABSTRACT

Provided herein are intermediates and processes useful for facile synthesis of compounds of Formula 2:

wherein $R^1$ is $C(O)R^2$; $R^2$ is alkyl optionally substituted with 1-5 halogens; G is phenyl or a 5-6 membered heteroaryl optionally substituted with 1-2 $R^3$; and each $R^3$ is independently $C_1$-$C_6$ alkyl, CN, $C_1$-$C_6$ alkyl-CN, 3-6 membered cycloalkyl, or 4-6 membered heterocycloalkyl.

14 Claims, No Drawings

SYNTHESIS OF HETEROCYCLIC COMPOUNDS

CROSS-REFERENCE TO RELATED PATENT APPLICATIONS

This application claims the benefit under 35 U.S.C. § 119(e) of U.S. Provisional application Ser. No. 63/017,587, filed Apr. 29, 2020, which is hereby incorporated by reference in its entirety.

FIELD

The present disclosure relates to heterocyclic compounds, methods for the preparation thereof, and compounds prepared employing same.

BACKGROUND

The compounds of this disclosure are potent inhibitors of mutated forms of c-Kit, and can be useful for treatment of c-Kit mutant mediated diseases, such as gastrointestinal stromal tumor (GIST) or mastocyctosis. The compound and its synthesis have been described in WO 2014/100620. There remains interest in developing other versatile and facile processes for the efficient preparation of this and other biologically active molecules, especially, on an industrial scale.

SUMMARY

In one embodiment, the present disclosure provides a compound of Formula 2:

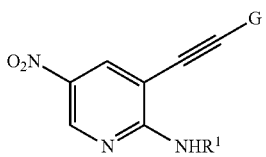

or a salt, a solvate, a tautomer, a stereoisomer, or a deuterated analog thereof, wherein:
$R^1$ is $C(O)R^2$;
$R^2$ is alkyl optionally substituted with 1-5 halogens;
G is phenyl or a 5-6 membered heteroaryl optionally substituted with 1-2 $R^3$; and
each $R^3$ is independently $C_1$-$C_6$ alkyl, CN, $C_1$-$C_6$ alkyl-CN, 3-6 membered cycloalkyl, or 4-6 membered heterocycloalkyl.

In another embodiment, the present disclosure provides a method for preparing a compound of Formula 2:

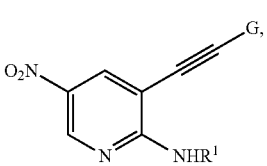

or a salt, a solvate, a tautomer, a stereoisomer, or a deuterated analog thereof, said method comprising:
contacting a compound of Formula (I) or a salt thereof:

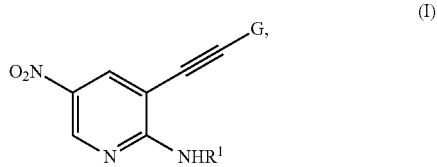

with an acetic anhydride, or a derivative thereof, to form the compound of Formula 2, wherein
$R^1$ is $C(O)R^2$;
$R^2$ is alkyl optionally substituted with 1-5 halogens;
G is phenyl or a 5-6 membered heteroaryl optionally substituted with 1-2 $R^3$; and
each $R^3$ is independently $C_1$-$C_6$ alkyl, CN, $C_1$-$C_6$ alkyl-CN, 3-6 membered cycloalkyl, or 4-6 membered heterocycloalkyl.

In another embodiment, the present disclosure provides a method for preparing a compound of Formula 3:

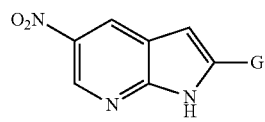

or a salt, a solvate, a tautomer, a stereoisomer, or a deuterated analog thereof, comprising:
contacting a compound of Formula (I) or a salt thereof:

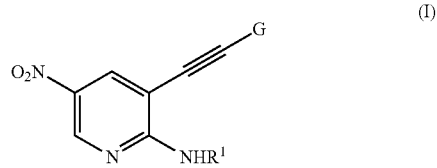

with an acetic anhydride, or a derivative thereof, to form the compound of Formula 2; and refluxing the compound of Formula 2 with an acetic anhydride, or a derivative thereof, in a suitable solvent to form a compound of Formula 3, wherein
$R^1$ is $C(O)R^2$;
$R^2$ is alkyl optionally substituted with 1-5 halogens;
G is phenyl or a 5-6 membered heteroaryl optionally substituted with 1-2 $R^3$; and
each $R^3$ is independently $C_1$-$C_6$ alkyl, CN, $C_1$-$C_6$ alkyl-CN, 3-6 membered cycloalkyl, or 4-6 membered heterocycloalkyl.

In yet another embodiment, the present disclosure provides a method for preparing a compound of Formula 4:

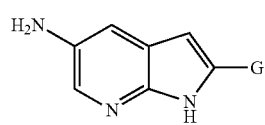

or a salt, a solvate, a tautomer, a stereoisomer, or a deuterated analog thereof, comprising: contacting a compound of Formula (I) or a salt thereof:

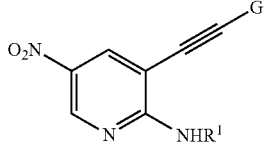

(I)

with an acetic anhydride, or a derivative thereof, to form the compound of Formula 2; refluxing a compound of Formula 2 with an acetic anhydride, or a derivative thereof, in a suitable solvent to form a compound of Formula 3; and reducing a compound of Formula 3 to form a compound of Formula 4, wherein $R^1$ is $C(O)R^2$;

$R^2$ is alkyl optionally substituted with 1-5 halogens;

G is phenyl or a 5-6 membered heteroaryl optionally substituted with 1-2 $R^3$; and each $R^3$ is independently $C_1$-$C_6$ alkyl, CN, $C_1$-$C_6$ alkyl-CN, 3-6 membered cycloalkyl, or 4-6 membered heterocycloalkyl.

In yet another embodiment, the present disclosure provides a method for preparing a compound of Formula 5:

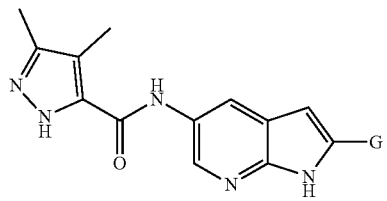

5 or a salt, a solvate, a tautomer, a stereoisomer, or a deuterated analog thereof, comprising: contacting a compound of Formula (I) or a salt thereof:

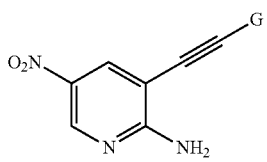

(I)

with an acetic anhydride, or a derivative thereof, to form the compound of Formula 2; refluxing a compound Formula 2 with an acetic anhydride, or a derivative thereof, in a suitable solvent to form a compound of Formula 3; reducing a compound of Formula 3 to form a compound of Formula 4; and combining a compound of Formula 4 with a compound of Formula 6:

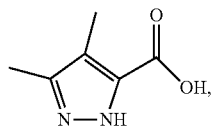

6 or a salt, a solvate, a tautomer, a stereoisomer, or a deuterated analog thereof with a suitable coupling agent to form a compound of Formula 5, wherein $R^1$ is $C(O)R^2$;

$R^2$ is alkyl optionally substituted with 1-5 halogens;

G is phenyl or a 5-6 membered heteroaryl optionally substituted with 1-2 $R^3$; and each $R^3$ is independently $C_1$-$C_6$ alkyl, CN, $C_1$-$C_6$ alkyl-CN, 3-6 membered cycloalkyl, or 4-6 membered heterocycloalkyl.

DETAILED DESCRIPTION

The present disclosure is related to novel synthetic intermediates and processes for the large-scale preparation of compounds of Formula 5:

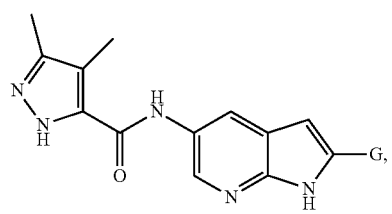

5 or a salt, a solvate, a tautomer, a stereoisomer, or a deuterated analog thereof, wherein:

G is phenyl or a 5-6 membered heteroaryl optionally substituted with 1-2 $R^3$, and each $R^3$ is independently $C_1$-$C_6$ alkyl, CN, $C_1$-$C_6$ alkyl-CN, 3-6 membered cycloalkyl, or 4-6 membered heterocycloalkyl.

In some embodiments, the salt of the compound of Formula 5 is a pharmaceutically acceptable salt thereof.

Advantageously, the present disclosure provides synthetic intermediates and versatile processes, which allow for high efficiency, low cost and large-scale facile synthesis of biologically active molecules with high purity.

Definitions

It is noted here that as used in this specification and the appended claims, the singular forms "a," "an," and "the" include plural reference unless the context clearly dictates otherwise.

The number of atoms in a group, exclusive of substitution, may be indicated as "x to y membered," "x-y membered," "$C_{x-y}$" or "$C_x$-$C_y$," wherein x is the minimum number of atoms in the group, and y is the maximum number of atoms in the group.

"Halogen" or "halo" refers to any halogen, including chloro (Cl), fluoro (F), bromo (Br), or iodo (I).

The term "alkyl," by itself or as part of another substituent, means, unless otherwise stated, a straight or branched chain hydrocarbon, having the number of carbon atoms designated (i.e. $C_{1-6}$ and $C_1$-$C_6$ mean one to six carbon atoms exclusive of substitution). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. When a prefix is not included to indicate the number of carbon atoms in an alkyl portion, the alkyl moiety or portion thereof will have 12 or fewer chain carbon atoms (comprising $C_{1-12}$ alkyl) or 8 or fewer chain carbon atoms (comprising $C_{1-8}$ alkyl) or 6 or fewer chain carbon atoms (comprising $C_{1-6}$ alkyl). For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-3}$ alkyl, and $C_{3-6}$ alkyl. "Fluoro substituted alkyl" denotes an alkyl group substituted with one or more fluoro, e.g., perfluoroalkyl, e.g., where preferably a lower alkyl is substituted with 1, 2, 3, 4 or 5 fluoro, or 1, 2, or 3 fluoro. While it is understood that substitutions are attached at any available atom to produce a stable compound, when optionally substituted alkyl is an R group of a moiety such as —OR (e.g. alkoxy), SR (e.g. thioalkyl), NHR (e.g. alkylamino), C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom).

"Cycloalkyl" refers to saturated or unsaturated, nonaromatic monocyclic, bicyclic or tricyclic carbon ring systems having the indicated number of ring atoms. A cycloalkyl may include, for example, 3-10, 3-8, or 3-6 ring atoms, such as cyclopropyl, cyclopentyl, cyclohexyl, 1-cyclohexenyl, adamantyl, and the like (e.g., $C_{3-8}$ cycloalkyl and 3-8 membered cycloalkyl mean ring systems having three to eight ring carbon atoms). "Cycloalkyl" or "carbocycle" include fused, bridged, and spiro bicyclic or polycyclic groups such as, for example, bicyclo[2.2.1]heptane, bicyclo[2.2.2]octane, etc. The cycloalkyl group may have one or more double or triple bond(s).

"Heteroaryl" refers to a monocyclic ring structure containing 5 or 6 ring atoms, or a bicyclic ring having 8 to 10 atoms, containing one or more, preferably 14, more preferably 13, even more preferably 12, ring heteroatoms independently selected from the group consisting of O, S, and N in which any ring is aromatic. Heteroaryl is also intended to include oxidized S or N, such as sulfinyl, sulfonyl and N-oxide of a tertiary ring nitrogen. A heteroaryl group can be attached to the remainder of the molecule through a ring carbon or a heteroatom. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalazinyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl, and thiadiazolyl. "Nitrogen containing heteroaryl" refers to heteroaryl wherein at least one ring heteroatom is N.

"Heterocycloalkyl" refers to a saturated or unsaturated non-aromatic cyclic group having a ring that contains from one to five heteroatoms, or 1 to 2 heteroatoms, independently selected from N, O, and S, wherein the nitrogen and sulfur atoms are optionally oxidized to form sulfinyl, sulfonyl and/or N-oxide of a tertiary ring nitrogen, and the nitrogen atom(s) are optionally quaternized, the remaining ring atoms being C, where one or two C atoms may optionally be present as a carbonyl. Heterocycloalkyl groups include those having a ring with a formally charge-separated aromatic resonance structure, for example, N-methylpyridonyl. The heterocycloalkyl may be a monocyclic, a bicyclic or a polycylic ring system of 3 to 12, 4 to 10 ring atoms, or 5 to 10 ring atoms, or 5 to 6 ring atoms. In some embodiments, the heterocycloalkyl includes one to five ring atoms or groups selected from —N=, —NH—, —O—, —S—, —S(O)—, or —S(O)$_2$— and —C(O)—. As an example, a 4-6 membered heterocycloalkyl is a heterocycloalkyl with 4-6 ring members having at least one heteroatom. Non limiting examples of heterocycloalkyl groups include pyrrolidinyl, piperidinyl, imidazolidinyl, pyrazolidinyl, butyrolactam, valerolactam, imidazolidinone, hydantoin, dioxolane, phthalimide, piperidine, 1,4-dioxane, morpholinyl, thiomorpholinyl, thiomorpholinyl-S-oxide, thiomorpholinyl-S,S-dioxide, piperazinyl, pyranyl, 3-pyrrolinyl, thiopyranyl, pyrone, tetrahydrofuranyl, tetrahydrothiophenyl, pyridone, quinuclidinyl, and the like. A heterocycloalkyl group can be attached to the remainder of the molecule through a ring carbon or a heteroatom.

The term "optionally substituted" refers to a group that may either be unsubstituted or substituted with the indicated substituent(s). Generally, substitution indicates that a hydrogen atom is replaced with the indicated group(s). In some embodiments, an optionally substituted group is unsubstituted. In some embodiments, an optionally substituted group is substituted with the indicated substituent(s).

"Protecting group" refers to a grouping of atoms that when attached to a reactive group in a molecule masks, reduces or prevents reactivity of the group. Examples of protecting groups can be found in T. W. Greene and P. G. Wuts, PROTECTIVE GROUPS IN ORGANIC CHEMISTRY, (Wiley, 4th ed. 2006), Beaucage and Iyer, Tetrahedron 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropyl silyl (TIPS), phenyl sulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

The term "leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy, trifluoroacetoxy), arylcarbonyloxy, mesyloxy, tosyloxy, trifluoromethanesulfonyloxy, aryloxy (e.g., 2,4-dinitrophenoxy, pentafluorophenoxy), methoxy, N,O-dimethyl-N-hydroxyamino, and the like.

The term "salt" is to be afforded its accepted meaning in the art and generally refers to a molecule that carries a charge, and which may be associated with a counter-ion. In certain embodiments, a salt of a given compound is a pharmaceutically acceptable salt.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphorsulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate:diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means a compound containing substituted deuterium atoms in place of hydrogen atoms. The deuterated analog of the disclosure may be a fully or partially deuterium substituted derivative.

In some embodiments, the deuterium substituted derivative of the disclosure holds a fully or partially deuterium substituted alkyl, aryl or heteroaryl group. When a compound is a deuterated analog, any substituent group (e.g., G, $R^1$, $R^2$, or $R^3$), or a combination of substituent groups, may include the designated number of deuterium atoms as replacing hydrogen atoms.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Unless otherwise stated, when a position is designated specifically as "H" or "hydrogen," the position is understood to have hydrogen at its natural abundance isotopic composition or its isotopes, such as deuterium (D) or tritium ($^3H$). Certain isotopically-labeled compounds of the present disclosure (e.g., those labeled with $^3H$ and $^{14}C$) are useful in compound and/or substrate tissue distribution assays. Tritiated (i.e., $^3H$) and carbon-14 (i.e., $^{14}C$) and fluorine-18 ($^{18}F$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

The term "conditions" in reference to a chemical reaction refers to the reaction environment and other factors affecting conduct of a chemical reaction. The term "under conditions sufficient to" or "under reaction conditions sufficient to"

refer to factors that bring about the indicated chemical conversion. Examples of reaction conditions include, but are not limited to, one or more of following: temperature, solvent, pH (e.g., as influenced by a discrete acidic or basic molecule), pressure, time, contact by a catalyst or promoter, ratios of reactants and/or catalysts, irradiation or lack thereof, etc. The conditions may be referred to by the intended conversion, such as, for example, coupling conditions, oxidation conditions, reduction conditions, etc. Exemplary reaction conditions sufficient to bring about the chemical conversions are provided herein. It is also contemplated that reaction conditions can include conditions, such as reagents, in addition to those described.

The term "tautomer" means compounds produced by the phenomenon wherein a proton of one atom of a molecule shifts to another atom without a change in the molecular formula. See, e.g., Jerry March, *Advanced Organic Chemistry; Reactions, Mechanisms and Structures*, Fourth Edition, John Wiley & Sons, pages 69-74 (1992). The term tautomer also refers to one of two or more interconverting structural isomers. Examples include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing at least two nitrogen atoms in which one nitrogen is present as an —NH—, such as pyrazoles, imidazoles, benzimidazoles, triazoles, and tetrazoles. The compounds described herein may have one or more tautomers. A person of ordinary skill in the art would recognize that other tautomeric rearrangements are possible. All such isomeric forms of a tautomeric compound are expressly included herein. Without limitation, tautomeric forms of 1H-pyrazoles and 2H-pyrazoles are contemplated.

A "stereoisomer" is a term for each of two or more compounds having the same molecular formula but differing in the spatial arrangement of the constituent atoms. The compounds of this disclosure may contain one or more asymmetric or chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, supercritical fluid chromathography, seeding with chiral crystals, chiral resolving agents, and the like.

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition, abbreviations as used herein have respective meanings as follows:

| | |
|---|---|
| ACN | Acetonitrile |
| AUC | Area under the curve |
| BOP | (Benzotriazol-1-yloxy)tris(dimethylamino)phosphonium hexafluorophosphate |
| COMU | (1-Cyano-2-ethoxy-2-oxoethylidenaminooxy)dimethylamino-morpholino-carbenium hexafluorophosphate |
| DIPA | Diisopropylamine |
| DMF | dimethylformamide |
| EtOAc | ethyl acetate |
| EtOH | Ethanol |
| ESI | Electrospray ionization |
| Et | ethyl |
| HATU | 1-[Bis(dimethylamino)methylene]-1H-1,2,3-triazolo[4,5-b]pyridinium 3-oxide hexafluorophosphate |
| HBTU | N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate |
| MeOH | Methanol |
| MS | Mass spectrometry |
| NMR | Nuclear magnetic resonance |
| NMP | N-methylpyrrolidone |
| Pd/C | Palladium on carbon |
| Ph | phenyl |
| PyBOP | (Benzotriazol-1-yloxy)tripyrrolidinophosphonium hexafluorophosphate |
| PyBrOP | Bromotripyrrolidinophosphonium hexafluorophosphate |
| TBTU | 2-(1H-Benzotriazole-1-yl)-1,1,3,3-tetramethylaminium tetrafluoroborate |
| TFA | Trifluoroacetic acid |
| TFAA | Trifluoroacetic anhydride |
| TFFH | Tetramethylfluoroformamidinium hexafluorophosphate |
| THF | Tetrahydrofuran |
| UPLC | Ultra performance liquid chromatography |

Compounds

In one embodiment, the present disclosure provides a compound of Formula 2:

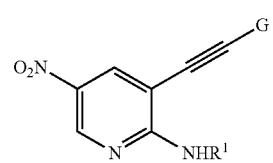

2 or a salt, a solvate, a tautomer, a stereoisomer, or a deuterated analog thereof, wherein:

$R^1$ is $C(O)R^2$;

$R^2$ is alkyl optionally substituted with 1-5 halogens;

G is phenyl or a 5-6 membered heteroaryl optionally substituted with 1-2 $R^3$; and each $R^3$ is independently $C_1$-$C_6$ alkyl, CN, $C_1$-$C_6$ alkyl-CN, 3-6 membered cycloalkyl, or 4-6 membered heterocycloalkyl.

In some embodiments, $R^2$ is $CF_3$.

In some embodiments, G is selected from phenyl, 4-cyano-2-methylphenyl, 1-methyl-1H-pyrazol-3-yl, 2-(4-morpholinyl)pyridin-4-yl, and 2-cyclopropylpyridin-4-yl.

In some embodiments, provided is a compound of Formula 2a:

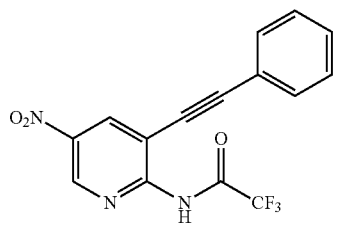

(2a)

or a salt, a solvate, a tautomer, a stereoisomer, or a deuterated analog thereof.

In some embodiments, provided is a compound of Formula 2e:

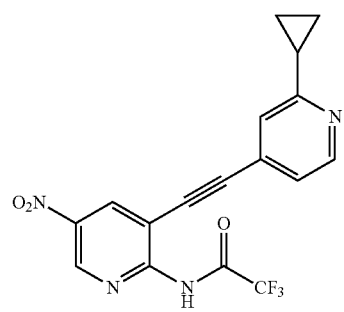

(2e)

or a salt, a solvate, a tautomer, a stereoisomer, or a deuterated analog thereof.

In some embodiments, the compound of Formula (I) is a compound of Formula (Ia), Formula (Ib), Formula (Ic), Formula (Id), or Formula (Ie):

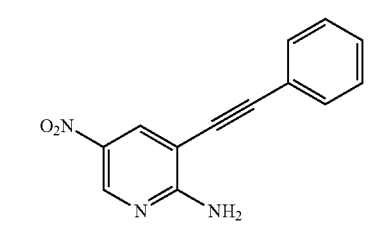

(Ia)

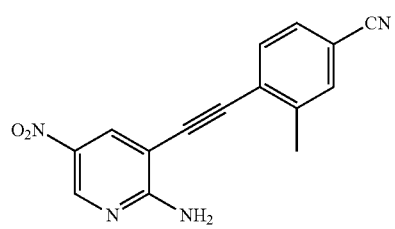

(Ib)

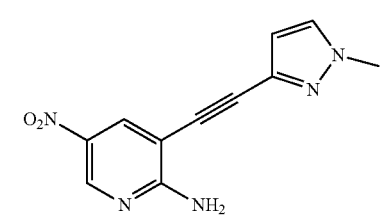

(Ic)

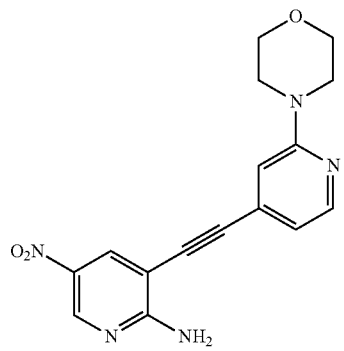

(Id)

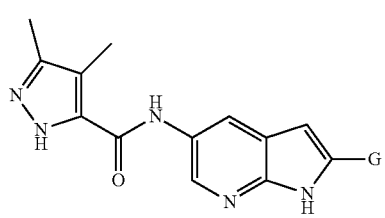

(Ie)

or a salt, a solvate, a tautomer, a stereoisomer, or a deuterated analog thereof.

The compounds of Formula 2 are useful intermediates for the synthesis of various biologically active molecules, for example, compounds of Formula 5:

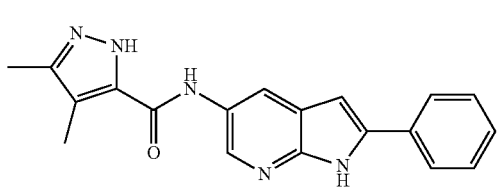

5 or a salt, a solvate, a tautomer, a stereoisomer, or a deuterated analog thereof, wherein G is as defined in this disclosure.

In some embodiments, the compound of Formula 5 is a compound of Formula 5a, Formula 5b, Formula 5c, Formula 5d, or Formula 5e:

5a

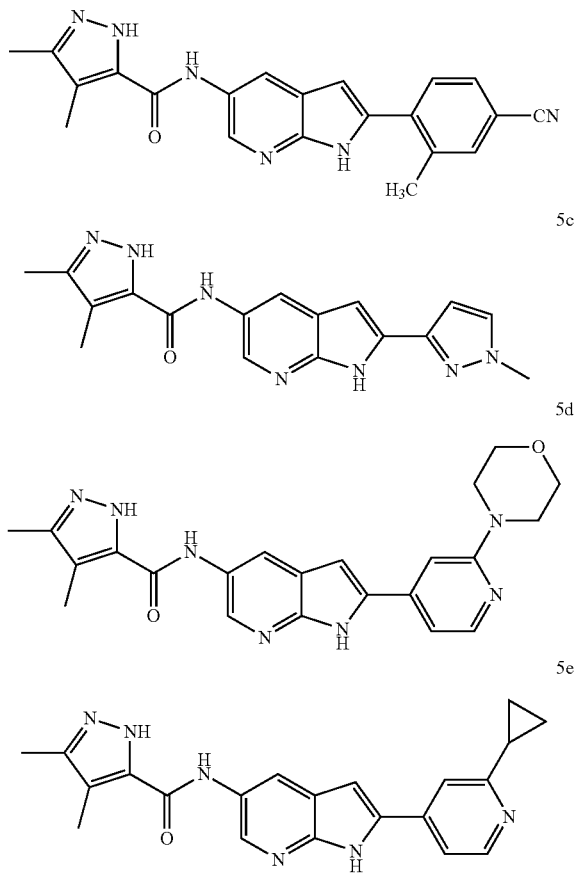

or a salt, a solvate, a tautomer, a stereoisomer, or a deuterated analog thereof. In some embodiments, the salt of the compound of Formula 5a, Formula 5b, Formula 5c, Formula 5d, or Formula 5e is a pharmaceutically acceptable salt.

Synthesis

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplemental (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like), where inert is taken to mean that no non-hydrogen atom of the solvent is incorporated in a substrate molecule. Unless specified to the contrary, the solvents used in the reactions of the present disclosure are inert organic solvents, and the reactions are carried out under an inert gas, preferably nitrogen.

It will also be appreciated that in each of the above schemes, the addition of any substituent may result in the production of a number of isomeric products (including, but not limited to, enantiomers or one or more diastereomers) any or all of which may be isolated and purified using conventional techniques. When enantiomerically pure or enriched compounds are desired, chiral chromatography and/or enantiomerically pure or enriched starting materials may be employed as conventionally used in the art or as described in the Examples.

Compounds of the present disclosure may be synthesized in accordance with the general reaction schemes and/or examples described below. The general schemes may be altered by substitution of the starting materials with other materials having similar structures to result in corresponding products. The structure of the desired product will generally make apparent to a person of skill in the art the required starting materials.

Scheme 1

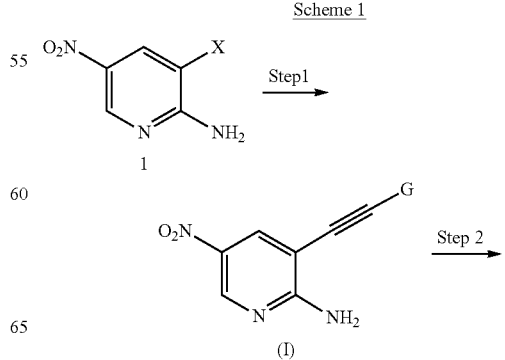

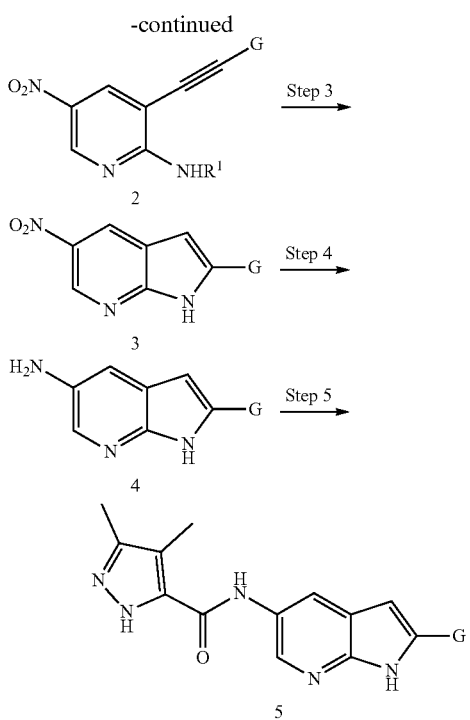

wherein G and X are as defined herein.

In Step 1, Formula (I) or a salt, a solvate, a tautomer, a stereoisomer, or a deuterated analog thereof, can be prepared by contacting Formula 1 or & salt thereof:

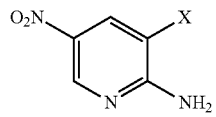

with a terminal alkyne ≡-G under conditions sufficient to form the compound of Formula (I) or a salt, a solvate, a tautomer, a stereoisomer, or a deuterated analog thereof, wherein X is a suitable leaving group and G is as described herein. In some embodiments, X is selected from Cl, Br, I, and a sulfonate (e.g., trifluoromethanesulfonate). In some embodiments, X is Br.

In Step 2, a compound of Formula 2 or a salt, a solvate, a tautomer, a stereoisomer, or a deuterated analog thereof can be prepared by contacting a compound of Formula (I) or a salt thereof:

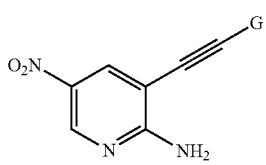

with an acetic anhydride, or a derivative thereof, under conditions sufficient to form the compound of Formula 2 or a salt, a solvate, a tautomer, a stereoisomer, or a deuterated analog thereof, wherein G is as described herein.

Non-limiting examples of acetic anhydride derivatives include trifluoroacetic anhydride, trichloroacetic anhydride, difluoroacetic anhydride, trifluoropropionic anhydride, pentafluoropropionic anhydride, and trifluoroacetic acetic anhydride. In some embodiments, the acetic anhydride derivative is trifluoroacetic anhydride.

In Step 3, a compound of Formula 3 or a salt, a solvate, a tautomer, a stereoisomer, or a deuterated analog thereof can be prepared by contacting a compound of Formula 2 or a salt thereof:

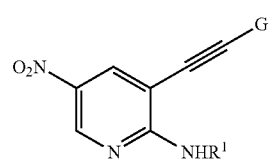

with an acetic anhydride, or a derivative thereof, under conditions sufficient to form a compound of Formula 3 or a salt, a solvate, a tautomer, a stereoisomer, or a deuterated analog thereof, wherein G is as described herein. Non-limiting examples of acetic anhydride derivatives include those provided herein.

The conditions sufficient to form a compound of Formula 3 or a salt, a solvate, a tautomer, a stereoisomer, or a deuterated analog thereof, may include a suitable solvent. Non-limiting examples of suitable solvents that can be employed include 2-methyltetrahydrofuran, isopropyl acetate, 1,4-dioxane, acetonitrile, and a mixture of acentonitrile (ACN)/N-methyl-2-pyrrolidone (NMP). In some embodiments, the conditions comprise a temperature of 70 to 90° C., or 81 to 85° C.

In some embodiments, Step 2 and Step 3 are performed in a one-pot process. In some embodiments, a compound of Formula 3 is prepared from a compound of Formula (I) in a process in which a compound of Formula 2 is not isolated. In some embodiments, Step 2 and/or Step 3 are performed in a copper-free process. In some embodiments of the one-pot process, a compound of Formula 2 or a salt thereof is contacted with an acetic anhydride, or a derivative thereof, under conditions sufficient to form a compound of Formula 3 or a salt, a solvate, a tautomer, a stereoisomer, or a deuterated analog thereof, wherein the conditions comprise an acid. In some embodiments, the acid is selected from acetic acid, formic acid, and trifluoroacetic acid. In some embodiments, the acid is trifluoroacetic acid. In some embodiments, the one-pot process conditions comprise trifluoroacetic acid, acetonitrile solvent, and heating to reflux.

In some embodiments, the acetic anhydride, or a derivative thereof, is used in 1 to 1.5 equivalents relative to a compound of Formula I and/or Formula 2. In some embodiments, the acetic anhydride, or a derivative thereof, is used in 1 to 1.2 equivalents relative to a compound of Formula I and/or Formula 2. In some embodiments, the acetic anhydride, or a derivative thereof, is used in 1 to 1.2 equivalents relative to a compound of Formula I and/or Formula 2. In some embodiments, trifluoroacetic anhydride (TFAA) is used in 1 to 1.2 equivalents relative to a compound of Formula I and/or Formula 2. In some embodiments, TFAA is used in about 1 equivalent relative to the compound of Formula I and/or Formula 2. In some embodiments, the conditions comprise trifluoroacetic acid, trifluoroacetic anhydride acetonitrile solvent, and heating to reflux.

In Step 4, Formula 4 or a salt, a solvate, a tautomer, a stereoisomer or a deuterated analog thereof can be prepared by reducing a compound of Formula 3, for example, by contacting a compound of Formula 3 or a salt thereof:

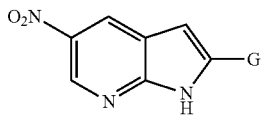

3 with a reducing agent under conditions sufficient to form the compound of Formula 4 or a salt, a solvate, a tautomer, a stereoisomer, or a deuterated analog thereof, wherein G is as described herein.

In some embodiments, the reducing agent is selected from Raney Ni, catalytic reduction (e.g., Pd/C and hydrogen), iron, zinc, and an aluminum hydride (e.g., lithium aluminum hydride). In some embodiments, the reducing agent is Pd/C and hydrogen at a pressure of atmosphere to 5000 psi. In some embodiments, the reducing agent is Pd/C and hydrogen at a pressure of 25 to 1000 psi, or 25 to 50 psi.

In Step 5, a compound of Formula 5 or a salt, a solvate, a tautomer, a stereoisomer or a deuterated analog thereof can be prepared by contacting a compound of Formula 4 or a salt thereof:

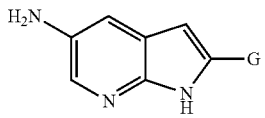

4 with a compound of Formula 6 or a salt thereof

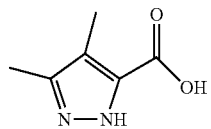

6 and a coupling agent under conditions sufficient to form the compound of Formula 5 or a salt, a solvate, a tautomer, a stereoisomer or a deuterated analog thereof, wherein G is as described herein. In some embodiments, a compound of Formula 6 is present as a tautomer. In some embodiments, the coupling conditions comprise a solvent, for example, dimethylsulfoxide or N,N-dimethylformamide, and a base, for example, triethylamine or diisopropylethylamine. In some embodiments, the coupling conditions comprise dimethylsulfoxide solvent. In particular, dimethylsulfoxide as a solvent in the coupling process facilitated reducing residual solvent of the compound of formula 5 to levels within ICH guidelines. For dimethylsulfoxide, the ICH guidelines permit 5000 ppm residual. In some embodiments, isolated Compound 5 comprises less than 5000 ppm dimethylsulfoxide.

Non-limiting examples of coupling agents that can be employed include BOP (benzotriazol-1-yloxytris(dimethylamino)phosphonium hexafluorophosphate), PyBOP (benzotriazol-1-yloxytripyrrolidinophosphonium hexafluorophosphate), PyBrOP (bromotripyrrolidinophosphonium hexafluorophosphate), TBTU (O-(benzotriazol-1-yl)-N,N,N',N'-tetramethyluronium tetrafluoroborate), HBTU (2-(1H-benzotriazol-1-yl)-1,1,3,3-tetramethyluronium hexafluorophosphate), HATU (1-[bis(dimethylamino)methylene]-1H-1,2,3-triazolo[4,5-b]pyridinium 3-oxide hexafluorophosphate), COMU ((1-cyano-2-ethoxy-2-oxoethylidenaminooxy)dimethylamino-morpholino-carbenium hexafluorophosphate), or TFFH (tetramethylfluoroformamidinium hexafluorophosphate). In another embodiment, the coupling agent is PyBOP.

The disclosure further provides a method for synthesis of a compound of Formula 3, Formula 4, and/or Formula 5, comprising a process:

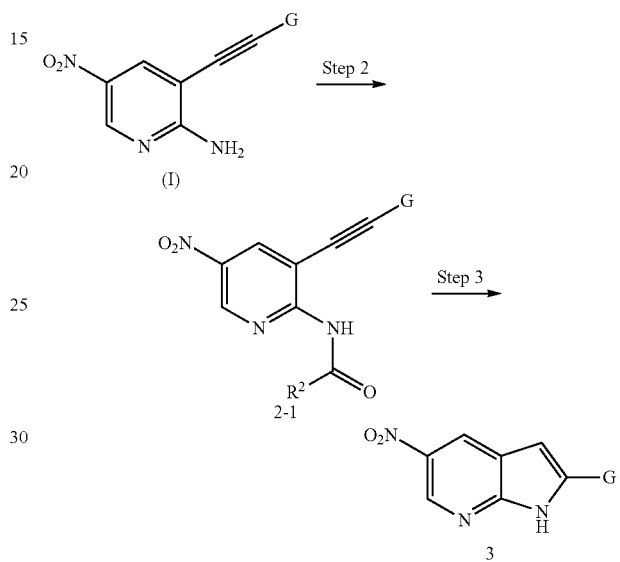

where G and $R^2$ are as defined herein.

It was discovered that, in the scheme above, the ability of the amine toward cyclization is increased by activating the amine with a trifluoroacetyl group. In one example, in Step 2, the trifluoroacetyl group is added to a compound of Formula (I) by contacting a compound of Formula (I) with trifluoroacetic anhydride (TFAA) in a suitable solvent, or both TFAA and trifluoroacetic acid (TFA) in a suitable solvent. Non-limiting examples of suitable solvents that can be employed in this embodiment include 2-methyltetrahydrofuran, isopropyl acetate, 1,4-dioxane, a mixture of acentonitrile (ACN)/N-methyl-2-pyrrolidone (NMP), trifluoroacetic acid, and acetonitrile. In some embodiments, the suitable solvent is acetonitrile. In another embodiment of Step 2, TFAA is added to a compound of Formula (I) in mixture of ACN/NMP to form a compound of Formula 2-1. In another embodiment of Step 2, TFAA is added to Formula (I) in a 1:1 molar mixture of ACN/NMP to form a compound of Formula 2-1. In another embodiment of Step 2, TFAA is added to a compound of Formula (I) in acetonitrile to form a compound of Formula 2-1. In another embodiment of Step 2, TFAA is added to a compound of Formula (I) in acetonitrile to form Formula 2-1. In another embodiment of Step 2, TFAA is added as a solution in acetonitrile. In some embodiments, Step 2 and Step 3 are performed concurrently without isolation of a compound of Formula 2-1.

In Step 3 of this disclosure, the formation of a compound of Formula 3 from a compound of Formula 2-1 can be accomplished by various conditions including reagents such as metal catalyzed reactions (copper, gold, palladium, zinc, etc.), or under basic conditions. In another embodiment, CuI is employed to catalyze the cyclization of a compound of Formula 2-1 to a compound of Formula 3.

However, it was discovered that using copper led to a difficult work-up, further complicated by the large amount of copper needed to ensure the reaction reached completion. The copper catalyzed reaction was found to be low yielding with an average yield of about 37% by weight. For CuI, it was found that these difficulties were primarily caused the metal catalyst, where copper had variability in loading due to its reduced efficacy in the presence of TFAA. This mandated unexpectedly high equivalents of CuI in the reaction, resulting in a higher level of impurities, and a difficult work-up to remove copper. Removing copper was important because copper was found to inhibit the reduction in the next step of converting the nitro group in Formula 3 to an amine in Formula 4.

Another embodiment relates to the conversion of Formula (I) directly to Formula 3 without employing a metal or base catalyst, and without isolating Formula 2-1. One example includes heating Formula I and acetic anhydride, or a derivative thereof, in a suitable solvent. For example the suitable solvent can be heated to reflux. Non-limiting examples of suitable solvents that can be employed in this embodiment include 2-methyltetrahydrofuran, isopropyl acetate, 1,4-dioxane, 1:1 acetonitrile/N-methyl-2-pyrrolidone and acetonitrile. In another embodiment, Formula (I) is converted to Formula 3 by contacting Formula (I) with TFAA in acetonitrile under reflux conditions. Optionally, acids can be added to facilitate this reaction. Non-limiting examples of acids that can be employed in this step include TFA, acetic acid (HOAc), and formic acid. In some embodiments, the acid is TFA. In another embodiment, Formula (I) is converted to Formula 3 using TFA and TFAA in acetonitrile under reflux conditions. Owing to the overwhelming amount of literature references that use metal catalysts such as CuI or bases for such cyclizations, it was surprising to see more successful results without the use of these catalysts. Additionally, Formula 3 was isolated in surprisingly higher yields compared to the catalyzed reaction using copper. In some embodiments, formation of Formula 3 proceeds at a yield of at least about 60%.

In another embodiment of Step 2 and Step 3, the temperature range and rate are chosen to add the majority of TFAA solution at a temperature below solvent reflux. In another embodiment of Step 2 and Step 3, 10% to 50% of TFAA is added at reflux to avoid precipitation of Formula 2-1. In another embodiment, of Step 3 the TFAA addition starts at about 40° C., and the temperature is increased at intervals of about 1.4° C. per minute to a final temperature of 80±10° C. In some embodiments, the final temperature is 83±2° C. In some embodiments, the final temperature is the reflux temperature of acetonitrile. It was found that the improved process provided Formula 3 in an isolated yield of at least 50% from Formula (I).

EXAMPLES

The following examples are offered to illustrate, but not to limit the subject matter described herein.

Certain molecules claimed in this disclosure can exist in different enantiomeric and diastereomeric forms and all such variants of these compounds are contemplated.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this disclosure. Further, the compounds are characterized using standard methods such as mass spectroscopy, nuclear magnetic resonance (NMR), etc. $^1$H Nuclear magnetic resonance (NMR) spectroscopy was carried out using a spectrometer operating at 300 MHz.

Example 1

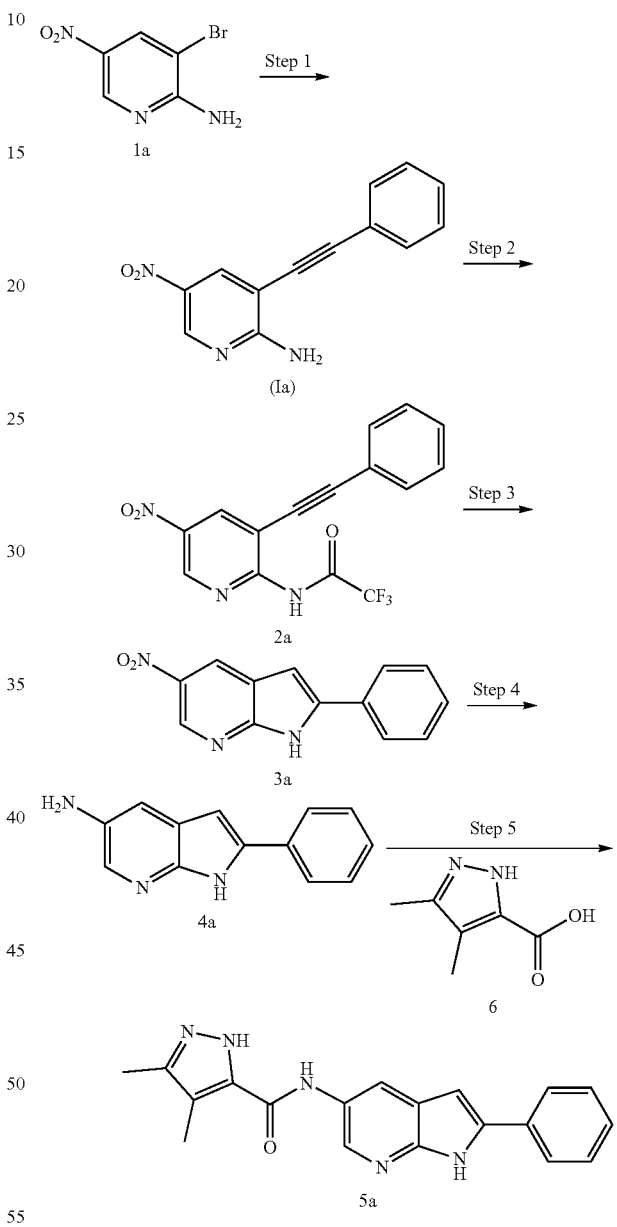

Step 1—Preparation of 5-nitro-3-(phenylethynyl)pyridin-2-amine (Ia)

A mixture of 3-bromo-5-nitro-pyridin-2-ylamine (1a, 2.18 g, 10.0 mmol), PdCl$_2$(PPh$_3$)$_2$ (0.071 g, 0.1 mmol), CuI (0.019 g, 0.1 mmol) in acetonitrile (4.4 mL) and DIPA (10.9 mL) was purged with argon at room temperature. A solution of ethynylbenzene (1.32 mL, 12.0 mmol) in ACN (2.2 mL) was added to the reaction mixture at 50° C. over 2 h. The reaction mixture was stirred at 50° C. for 16 h, and then cooled to 10° C. The solid was collected by filtration, and washed with MeOH—H$_2$O (3:1) and then with MeOH. The solid was dried under vacuum to furnish pure 5-nitro-3-(phenylethynyl)pyridin-2-amine Ia (2.126 g, 89% yield).

Step 2—Preparation of 2,2,2-trifluoro-N-(5-nitro-3-(phenylethynyl)pyridin-2-yl)acetamide (2a)

To a solution of 5-nitro-3-(phenylethynyl)pyridin-2-amine (Ia, 1.0 g, 4.18 mmol) in acetonitrile (20 mL) was added TFAA (0.65 mL, 4.60 mmol) at 30° C. The reaction was stirred at the same temperature for 1 h, and then cooled to 0° C. The solid was collected by filtration and dried under vacuum to furnish 2,2,2-trifluoro-N-(5-nitro-3-(phenylethynyl)pyridin-2-yl)acetamide 2a (0.602 g, 43% yield).

Step 3—Preparation of 5-nitro-2-phenyl-1H-pyrrolo[2,3-b]pyridine (3a)

To a solution of 2,2,2-trifluoro-N-(5-nitro-3-(phenylethynyl)pyridin-2-yl)acetamide (2a, 0.602 g, 1.796 mmol) in NMP (6.6 mL), was added CuI (0.034 g, 0.18 mmol). The reaction was stirred under an argon atmosphere for 16 h at 90° C. The cooled reaction mixture was poured into water (30 mL), and the precipitate was collected by filtration. The solid was purified by silica gel chromatography using 0-20% DCM-ethyl acetate. The isolated solid was triturated with ethyl acetate to furnish 5-nitro-2-phenyl-1H-pyrrolo[2,3-b]pyridine 3a (182 mg, 42% yield).

Step 4—Preparation of 2-phenyl-1H-pyrrolo[2,3-b]pyridin-5-amine (4a)

To a solution of 5-nitro-2-phenyl-1H-pyrrolo[2,3-b]pyridine (3a, 0.182 g, 0.761 mmol) in tetrahydrofuran (30 mL) was added 5% palladium on carbon (0.12 g). The reaction mixture was stirred under 1 atm of hydrogen for 3 h. The catalyst was filtered off, and the filtrate was concentrated under reduced pressure to furnish 2-phenyl-1H-pyrrolo[2,3-b]pyridin-5-amine 4a (160 mg, 100% yield).

Step 5—Preparation of 4,5-dimethyl-N-(2-phenyl-1H-pyrrolo[2,3-b]pyridin-5-yl)-1H-pyrazole-3-carboxamide (5a)

To a solution of 2-phenyl-1H-pyrrolo[2,3-b]pyridin-5-ylamine (4a, 0.160 g, 0.765 mmol), 4,5-dimethyl-2H-pyrazole-3-carboxylic acid (6, 0.118 g, 0.841 mmol) and diisopropylethylamine (0.16 mL, 0.918 mmol) in N,N-dimethylformamide (10 mL), was added a solution of PyBOP (0.437 g, 0.841 mmol) in N,N-dimethylformamide (5 mL) dropwise at 0° C. The reaction was stirred at 0° C. for 3 h, and then at room temperature overnight. The reaction mixture was poured into water (15 mL), and the precipitate was collected by filtration. The solid was triturated with acetone and ethyl acetate, and collected by filtration to furnish 4,5-dimethyl-N-(2-phenyl-1H-pyrrolo[2,3-b]pyridin-5-yl)-1H-pyrazole-3-carboxamide 5a (179 mg, 70% yield).

Step 2 and Step 3—Improved Preparation of 5-nitro-2-phenyl-1H-pyrrolo[2,3-b]pyridine (3a)

To a solution of 5-nitro-3-(phenylethynyl)pyridin-2-amine (Ia) in acetonitrile (30 volumes) was added TFA (1 equivalent). The mixture was heated to reflux and TFAA (1.2 equivalents) in 1 volume of acetonitrile was added slowly over 40 minutes while the reaction was held at reflux. 5-nitro-2-phenyl-1H-pyrrolo[2,3-b]pyridine (3a) was isolated in 60% yield in a purity of 99% AUC (UPLC).

Step 2 and Step 3—Second Improved Preparation of 5-nitro-2-phenyl-1H-pyrrolo[2,3-b]pyridine (3a)

To a solution of 5-nitro-3-(phenylethynyl)pyridin-2-amine (Ia, 100.0 g, 1 equivalent) in acetonitrile (1.4 L, 14 volumes) was added TFA (24 mL, 0.31 mol, 0.75 equivalents) in one portion. The mixture was slowly heated, and at 40° C. a solution of TFAA (61.9 mL, 0.44 mol, 1.05 equivalents) in acetonitrile (100 mL, 1 volume) was added over 40 minutes during which time the mixture reached 82° C. The reaction was stirred at reflux for 48 hours, during which time an additional aliquot of TFA (8 mL, 1 equivalent) was added in one portion. The reaction was monitored for an additional 72 h, during which time an additional aliquot of TFA was added (0.25 equivalents). The reaction mixture was cooled to room temperature and stirred for an additional 38 h. The mixture was filtered, washed with methanol (3×80 mL), and dried under vacuum at 70° C. for 20 h. 5-nitro-2-phenyl-1H-pyrrolo[2,3-b]pyridine 3a was isolated in 64% yield.

Step 4—Improved Preparation of 2-phenyl-1H-pyrrolo[2,3-b]pyridin-5-amine (4a)

To a solution of 5-nitro-2-phenyl-1H-pyrrolo[2,3-b]pyridine (3a, 54.0 g, 1 equivalent) in tetrahydrofuran (594 mL, 11 volumes) in a stainless steel autoclave was added 5% palladium on carbon (5.4 g, 10 wt %) and dimethylformamide (27 mL, 0.5 volumes) as a rinse. Ethanol (486 mL, 9 volumes) was then added. The reaction was purged with nitrogen and charged with 2 bar of hydrogen, set to 25° C. for 1 h, then heated to 40° C. and stirred for 1 h, then hydrogen pressure was increased to 3 bar, temperature was reduced to 20° C. and the reaction was stirred overnight. An additional 6.4 volumes of tetrahydrofuran was then added and the reaction was stirred at 40° C. for 30 minutes. The catalyst was filtered over celite to remove the catalyst, and the filtrate was concentrated under reduced pressure to 5 volumes, diluted with 4 volumes of toluene, concentrated again to 5 volumes, diluted with an additional 4 volumes of toluene, and filtered to furnish a solid, which was washed with toluene (2×3 volumes) and dried to provide the product 2-phenyl-1H-pyrrolo[2,3-b]pyridin-5-amine 4a (93% yield).

Step 5—Improved Preparation of 4,5-dimethyl-N-(2-phenyl-1H-pyrrolo[2,3-b]pyridin-5-yl)-1H-pyrazole-3-carboxamide (5a)

To a solution of 2-phenyl-1H-pyrrolo[2,3-b]pyridin-5-ylamine (4a, 0.191 mol, 1 equivalent), 4,5-dimethyl-2H-pyrazole-3-carboxylic acid (6, 0.229 mol, 1.2 equivalents) and diisopropylethylamine (43.3 mL, 0.249 mol, 1.3 equivalents) in dimethylsulfoxide (360 mL, 9 volumes), and the mixture was adjusted to 18° C. A solution of PyBOP (0.229 mol) in dimethylsulfoxide (240 mL, 6 volumes) over 50 minutes, at which time the reaction temperature did not exceed 21° C. The reaction mixture was stirred at 18° C. for 1.5 h. The reaction mixture was polish filtered and 15 volumes of dichloromethane was added, the mixture was stirred for 3 hours, and the solid was collected. The filter cake was washed with DCM and the solid was dried on the filter for 1 h, then dried under vacuum at 60° C. for 20 h to furnish 4,5-dimethyl-N-(2-phenyl-1H-pyrrolo[2,3-b]pyridin-5-yl)-1H-pyrazole-3-carboxamide 5a (57% yield).

Example 2

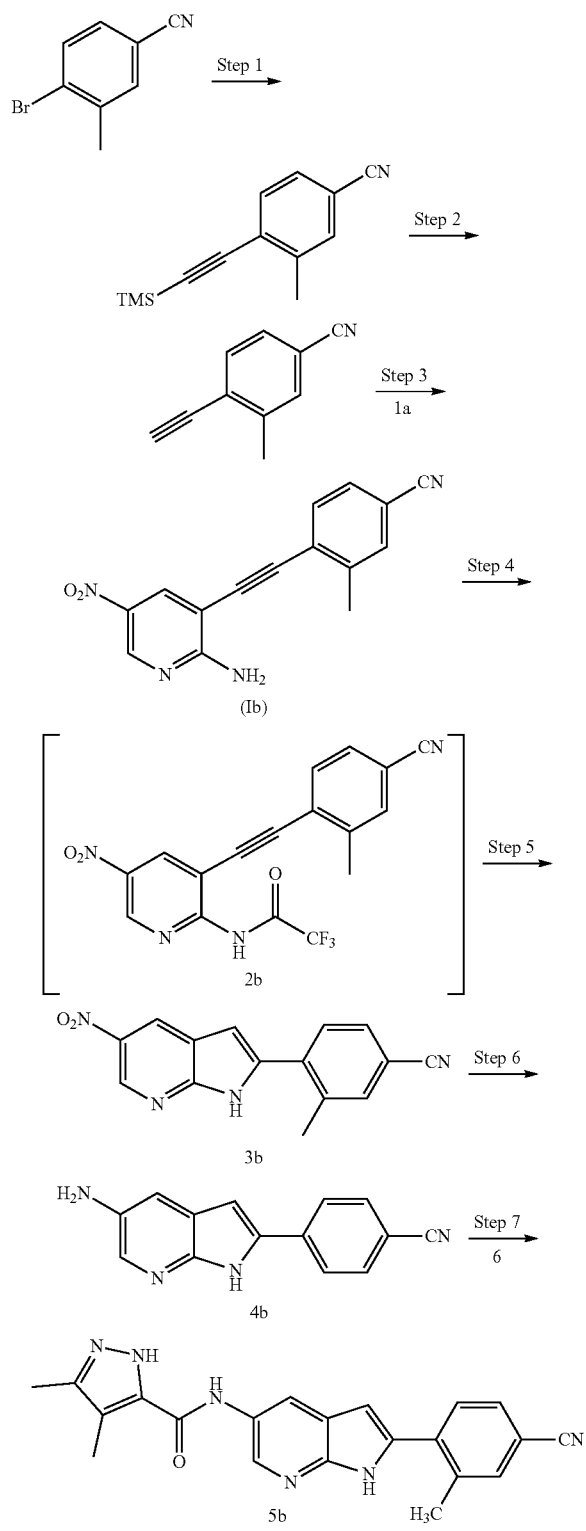

Step 1—Preparation of 3-methyl-4-((trimethylsilyl)ethynyl)benzonitrile

Into a solution of 4-bromo-3-methylbenzonitrile (6.13 g, 31.28 mmol) in anhydrous THF (100 mL) were added CuI (298 mg, 1.564 mmol), PdCl$_2$(PPh$_3$)$_2$ (1.10 g, 1.564 mmol) and Et$_3$N (6.33 g, 8.7 mL, 62.56 mmol). The reaction solution was purged with argon for 10 min, at which time ethynyltrimethylsilane (15.36 g, 22 mL, 0.156 mol) was added. The reaction mixture was heated at 70° C. under argon for 16 h and then cooled to room temperature. Saturated ammonium chloride aqueous solution (100 mL) was added, and the organic layer was separated. The aqueous layer was extracted with ether (3×200 mL), and the combined organic layers were washed with brine, dried over magnesium sulfate, filtered and concentrated. The residue obtained was purified by ISCO silica gel chromatography using 0-30% dichloromethane in hexane to afford 3-methyl-4-(2-trimethylsilyl)ethynyl)benzonitrile (6.43 g, 96% yield). ESI-MS m/z calc. 213.1 found 214.3 (MTH)+.

Step 2—Preparation of 4-ethynyl-3-methylbenzonitrile

To a solution of 3-methyl-4-(2-trimethylsilyl)ethynyl)benzonitrile (6.43 g, 30.13 mmol) in methanol (100 mL) was added K$_2$CO$_3$ (8.32 g, 60.26 mmol). The resulting solution was stirred for 1 h at room temperature. All solvents were removed under reduced pressure, and the residue so obtained was partitioned between ether (300 mL), and water (150 mL). The organic layer was separated and the aqueous layer was extracted with ether (2×100 mL). The combined organic layers were washed with saturated aqueous sodium bicarbonate solution (50 mL), brine (50 mL), dried over magnesium sulfate, filtered and concentrated under reduced pressure. The residue was purified by ISCO silica gel chromatography using 0-30% dichloromethane in hexane to afford 4-ethynyl-3-methylbenzonitrile (3.82 g, 90% yield). ESI-MS m/z calc. 141.1 found 141.8 (M+H)+.

Step 3—Preparation of 4-((2-amino-5-nitropyridin-3-yl)ethynyl)-3-methylbenzonitrile (Ib)

4-Ethynyl-3-methylbenzonitrile (1.07 g, 7.59 mmol), 3-bromo-5-nitropyridin-2-amine (1a, 1.38 g, 6.33 mmol), PdCl$_2$(PPh$_3$)$_2$ (44.4 mg, 0.0633 mmol) and CuI (12 mg, 0.0633 mmol) were dissolved in a mixture of CH$_3$CN (12 mL) and i-Pr$_2$NH (30 mL). The solution was purged with argon for 5 min, then heated at 52° C. under argon for 24 h. LCMS analysis indicated incomplete reaction. The reaction mixture was then heated at 80° C. for an additional 16 h. The reaction solution was cooled to room temperature, filtered, washed with acetonitrile (6 mL), MeOH/H$_2$O (3/1, 2×18 mL) followed by MeOH (12 mL). The solid obtained was then dried under high vacuum at 60° C. to afford 4-(2-(2-amino-5-nitropyridin-3-yl)ethynyl)-3-methylbenzonitrile Ib (949 mg, 54% yield). ESI-MS m/z calc. 278.1 found 279.0 (M+H)+.

Steps 4 and 5—Preparation of 3-Methyl-4-(5-nitro-1H-pyrrolo[2,3-b]pyridine-2-yl)benzonitrile (3b)

To a solution of 4-(2-(2-amino-5-nitropyridin-3-yl)ethynyl)-3-methylbenzonitrile (Ib, 945 mg, 3.40 mmol) in a mixture of NMP (7.5 mL) and CH$_3$CN (7.5 mL) was added TFAA (784 mg, 3.74 mmol) at 0° C. The resulting solution was stirred at this temperature for 30 min. After the reaction was complete, most of the acetonitrile was removed under reduced pressure. Acetonitrile (4.5 mL) was added, and concentrated again under reduced pressure until the volume of solution was about 7.5 mL. To this solution was added CuI (65 mg, 0.34 mmol) and NMP (7.5 mL). The reaction mixture was heated at 90-95° C. for 40 h and then cooled to room temperature. Saturated aqueous ammonium chloride solution (50 mL) and 2-methyltetrahydrofuran (100 mL) were added. The mixture was sonicated for 20 min, filtered, washed with saturated aqueous ammonium chloride solution containing 1% ammonium hydroxide (50 mL), water (50 mL) and hexane. The solid so obtained was dried under high vacuum at 60° C. to afford 3-methyl-4-(5-nitro-1H-pyrrolo[2,3-b]pyridine-2-yl)benzonitrile 3b (549 mg, 58% yield). ESI-MS m/z calc. 278.1 found 279.1 (M+H)+.

Step 6—Preparation of 4-(5-Amino-1H-pyrrolo[2,3-b]pyridine-2-yl)-3-methylbenzonitrile (4b)

To a solution of 3-methyl-4-(5-nitro-1H-pyrrolo[2,3-b]pyridine-2-yl)benzonitrile (538 mg, 1.93 mmol) in a mixture of ethanol (120 mL) and tetrahydrofuran (120 mL) was added 5% Pd on carbon (110 mg). The resulting suspension was hydrogenated in a Parr shaker at 60 psig for 16 h. The solution was filtered through Celite, washing the filter cake with THF. The filtrate was concentrated under reduced pressure, and the solid so obtained was suspended in ethanol (5 mL), sonicated for 10 min and filtered to afford 4-(5-amino-1H-pyrrolo[2,3-b]pyridine-2-yl)-3-methylbenzonitrile 4b (100 mg, 21% yield). ESI-MS m/z calc. 248.1 found 249.2 (M+1)+.

Step 7—Preparation of N-(2-(4-Cyano-2-methylphenyl)-1H-pyrrolo[2,3-b]pyridin-5-yl)-3,4-dimethyl-1H-pyrazole-5-carboxamide (5b)

To a solution of 4-(5-amino-1H-pyrrolo[2,3-b]pyridine-2-yl)-3-methylbenzonitrile (4b, 100 mg, 0.403 mmol) and 3,4-dimethyl-1H-pyrazole-5-carboxylic acid (6, 56.5 mg, 0.403 mmol) in anhydrous DMF (2 mL) was added diisopropylethylamine (57.3 mg, 77.2 µl, 0.443 mmol). The solution was cooled to 0° C., and PyBOP (220 mg, 0.423 mmol) was added. The resulting mixture was stirred at ambient temperature for 16 h. Ethyl acetate (4 mL) was added, the mixture was sonicated, filtered, and washed with water (10 mL) and hexane. The material so obtained was dried under high vacuum at 60° C. to afford A-(2-(4-cyano-2-methylphenyl)-1H-pyrrolo[2,3-b]pyridin-5-yl)-3,4-dimethyl-1H-pyrazole-5-carboxamide 5b (70 mg, 47% yield). ESI-MS m/z calc. 370.2 found 371.1 (M+1)+. ¹HNMR (250 MHz, DMSO-d6) δ (ppm): 12.93 (s, 1H), 12.00 (s, 1H), 10.00 (s, 1H), 8.59 (s, 1H), 8.43 (s, 1H), 7.96-7.78 (m, 3H), 6.75 (s, 1H), 2.55 (s, 3H), 2.21 (s, 3H), 2.19 (s, 3H).

Example 3

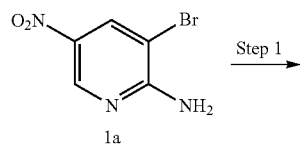

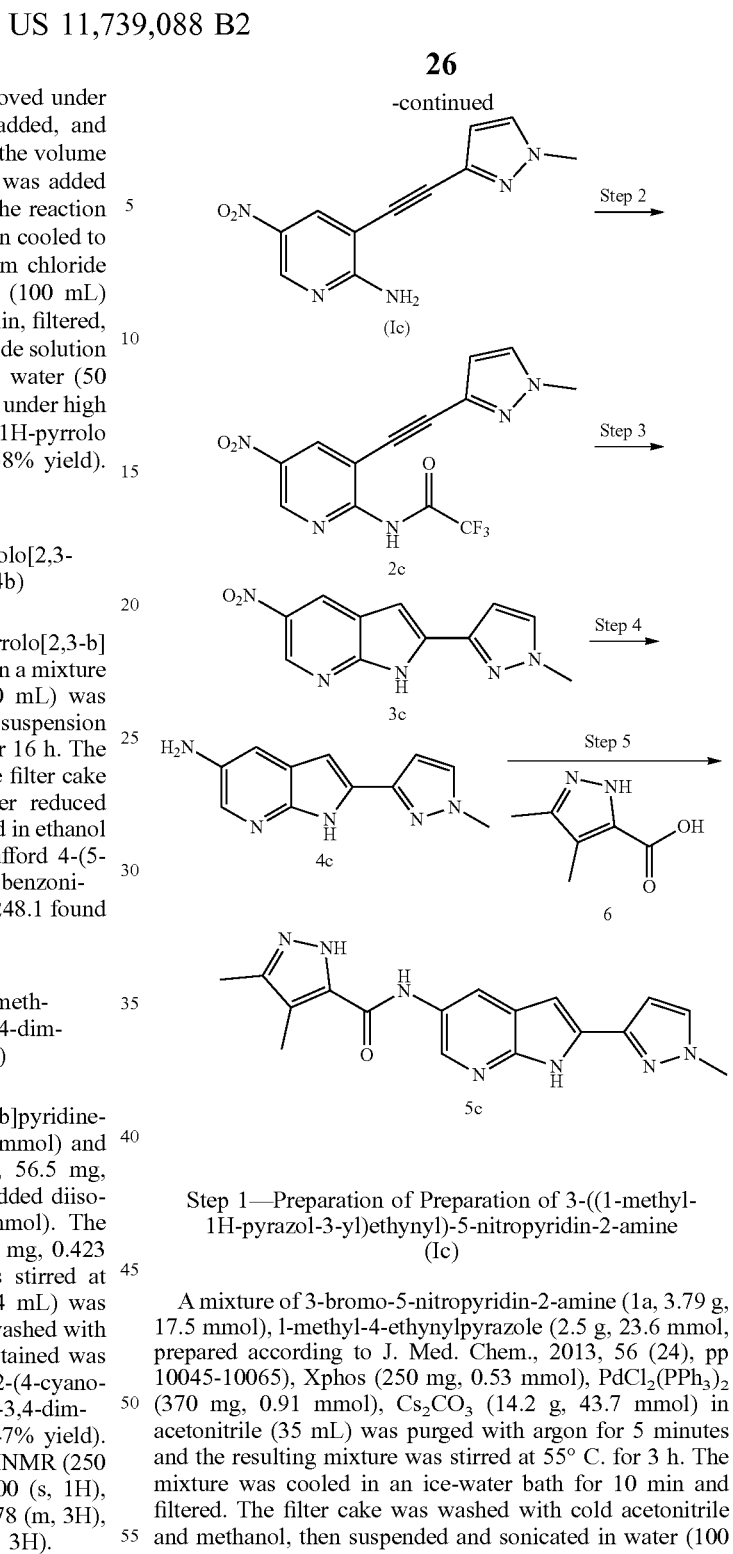

Step 1—Preparation of Preparation of 3-((1-methyl-1H-pyrazol-3-yl)ethynyl)-5-nitropyridin-2-amine (Ic)

A mixture of 3-bromo-5-nitropyridin-2-amine (1a, 3.79 g, 17.5 mmol), 1-methyl-4-ethynylpyrazole (2.5 g, 23.6 mmol, prepared according to J. Med. Chem., 2013, 56 (24), pp 10045-10065), Xphos (250 mg, 0.53 mmol), PdCl₂(PPh₃)₂ (370 mg, 0.91 mmol), Cs₂CO₃ (14.2 g, 43.7 mmol) in acetonitrile (35 mL) was purged with argon for 5 minutes and the resulting mixture was stirred at 55° C. for 3 h. The mixture was cooled in an ice-water bath for 10 min and filtered. The filter cake was washed with cold acetonitrile and methanol, then suspended and sonicated in water (100 mL). The solid was collected by filtration and washed with some cold acetonitrile and methanol to give 3-((1-methyl-1H-pyrazol-3-yl)ethynyl)-5-nitropyridin-2-amine Ic (4.3 g, 100% yield). ESI-MS m/z calc. 243.08 found 244.1 (M+H)+.

Step 2—Preparation of 2,2,2-trifluoro-N-(3-((1-methyl-1H-pyrazol-3-yl)ethynyl)-5-nitro-pyridin-2-yl)acetamide (2c)

To a solution of 3-((1-methyl-1H-pyrazol-3-yl)ethynyl)-5-nitropyridin-2-amine (Ic, 4.05 g, 16.66 mmol) in a 1:1 mixture of acetonitrile:NMP (18:18 mL) was added TFAA (2.9 mL, 20.53 mmol) dropwise over 10 min, and the reaction mixture was stirred at room temperature for 3 h. The mixture was concentrated to remove acetonitrile, and then diluted with cold water (200 mL). The precipitate thus formed was collected by filtration to afford 2,2,2-trifluoro-N-(3-((1-methyl-1H-pyrazol-3-yl)ethynyl)-5-nitropyridin-2-yl)acetamide 2c (5.15 g, 74% yield). ESI-MS m/z calc. 339.06 found 340.0 (M+H)+.

Step 3—Preparation of 2-(1-methyl-1H-pyrazol-3-yl)-5-nitro-1H-pyrrolo[2,3-b]pyridine (3c)

A mixture of 2,2,2-trifluoro-N-(3-((1-methyl-1H-pyrazol-3-yl)ethynyl)-5-nitropyridin-2-yl)-acetamide (2c, 5.03 g, 14.8 mmol) and CuI (0.422 g, 2.22 mmol) in NMP (20 mL) was stirred at 74° C. for 4 h. The cooled reaction mixture was poured into a solution of 10% NH$_4$Cl aqueous solution (120 mL) and 28% NH$_4$OH (20 mL) and the mixture was stirred at room temperature for 5 h. The solid thus formed was collected by filtration and washed with water and methanol to give 2-(1-methyl-1H-pyrazol-3-yl)-5-nitro-1H-pyrrolo[2,3-b]pyridine (2.25 g, 63% yield) 3c. ESI-MS m/z calc. 234.08, found 244.2 (M+H)+.

Step 4—Preparation of 2-(1-methyl-1H-pyrazol-3-yl)-1H-pyrrolo[2,3-b]pyridin-5-amine (4c)

To a solution of 2-(1-methyl-1H-pyrazol-3-yl)-5-nitro-1H-pyrrolo[2,3-b]pyridine (3c, 1 g, 4.12 mmol) in tetrahydrofuran (20 mL) and DMF (7 mL) was added 5% Pd/C (250 mg) and the mixture was hydrogenated in a Parr shaker at 45 psig for 18 h. The Pd catalyst was filtered off and the reaction mixture was concentrated to remove all solvents. Diethyl ether (10 mL) was added and the solid thus formed was collected by filtration to give 2-(1-methyl-1H-pyrazol-3-yl)-1H-pyrrolo[2,3-b]pyridin-5-amine 4c (0.84 g, 96% yield). ESI-MS m/z calc. 213.1, found 214.0 (M+H)+.

Step 5—Preparation of 3,4-dimethyl-N-(2-(1-methyl-1H-pyrazol-3-yl)-1H-pyrrolo[2,3-b]-pyridin-5-yl)-1H-pyrazole-5-carboxamide (5c)

A solution of 2-(1-methyl-1H-pyrazol-3-yl)-1H-pyrrolo[2,3-b]pyridin-5-amine (4c, 0.72 g, 3.38 mmol), 3,4-dimethyl-1H-pyrazole-5-carboxylic acid (6, 0.54 g, 3.88 mmol) and BOP (1.715 g, 3.88 mmol) in DMF (6 mL) was cooled in an ice-water bath. Diisopropylethylamine (0.8 mL, 4.56 mmol) was added dropwise and the reaction mixture was stirred at room temperature for 6 h, at which time the reaction was charge with another equivalent of BOP, 3,4-dimethyl-1H-pyrazole-5-carboxylic acid 6 and diisopropylethylamine at 0-5° C. and was stirred for 4 h. Repeated additions were done until full consumption of the starting amine was observed. The reaction mixture was poured into water (60 mL) and collected by filtration. The material was washed with MeOH and diethyl ether to afford 3,4-dimethyl-N-(2-(1-methyl-1H-pyrazol-3-yl)-1H-pyrrolo[2,3-b]pyridin-5-yl)-1H-pyrazole-5-carboxamide 5c (409 mg, 36.1% yield). ESI-MS m/z calc. 335.15, found 336.2 (M+H)+.

Example 4

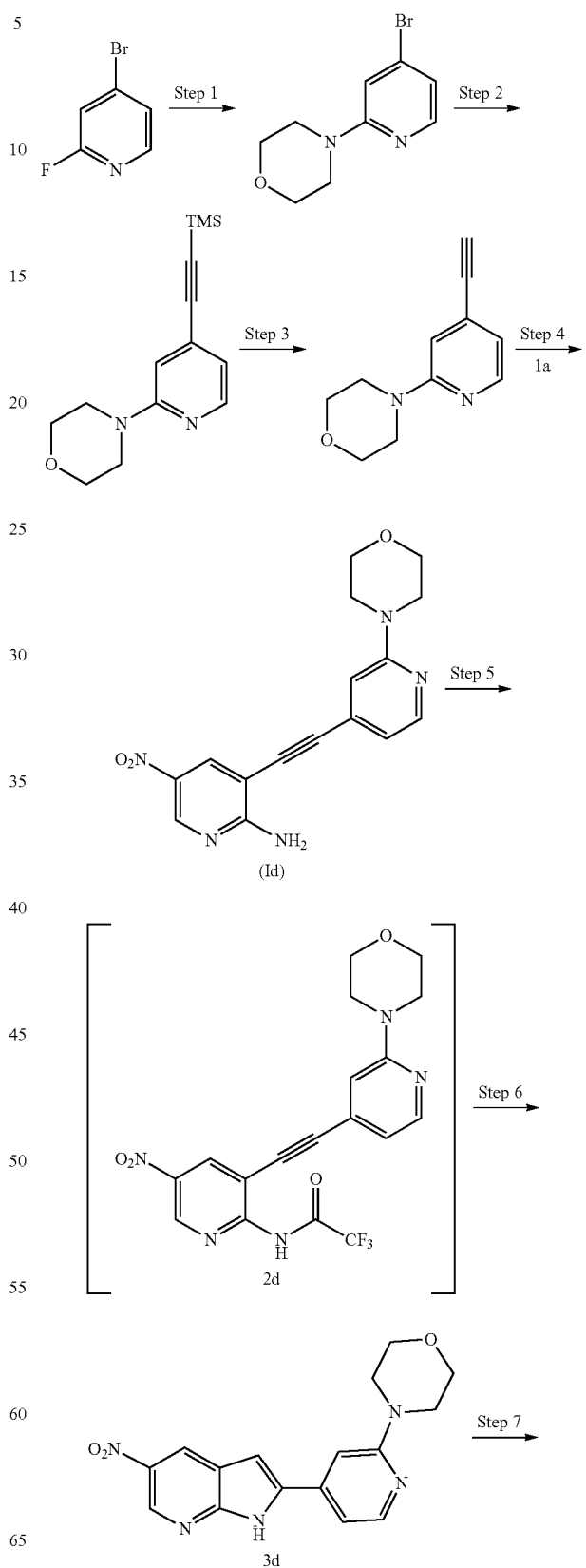

-continued

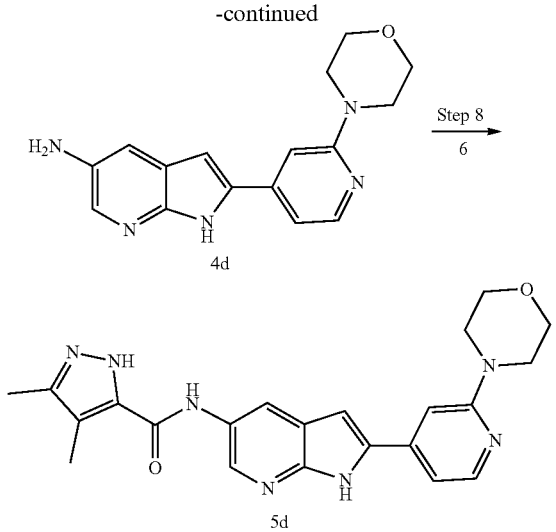

Step 1—Preparation of 4-(4-bromopyridin-2-yl)morpholine

A mixture of 4-bromo-2-fluoropyridine (3.1 mL, 30.0 mmol), morpholine (2.6 mL, 30.0 mmol) and potassium carbonate (4.15 g, 30.0 mmol) in DMF (30 mL) is heated at 100° C. overnight under nitrogen. The DMF was removed under reduced pressure and EtOAc (100 mL) was added. The reaction is washed with water (50 mL) and brine (25 mL). The organic layer was dried over sodium sulfate and concentrated. The crude residue was purified by silica gel column chromatography using 0-20% hexanes-EtOAc to give 4-(4-bromopyridin-2-yl)morpholine (5.56 g, 72% yield). ESI-MS m/z calc. 242.01, found 243.0 (M+H)+.

Step 2—Preparation of 4-(4-((trimethylsilyl)ethynyl)pyridin-2-yl)morpholine

A mixture of 4-(4-bromopyridin-2-yl)morpholine (5.32 g, 21.9 mmol), PdCl2(PPh3)2 (768 mg, 1.09 mmol), copper iodide (207 mg, 1.09 mmol), triethylamine (5.8 mL, 42.0 mmol) and TMS-acetylene (15.0 mL, 109.5 mmol) in THF (42 mL) under nitrogen was heated at 70° C. for 1 h. EtOAc (100 mL) was added and the reaction mixture was washed with water (50 mL) and brine (50 mL). After removal of the solvent, the crude residue was purified by silica gel column chromatography using 0-30% hexanes:EtOAc to give 4-(4-((trimethylsilyl)ethynyl)pyridin-2-yl)morpholine (5.96 g, 100% yield). ESI-MS m/z calc. 260.13, found 261.1 (M+H)+.

Step 3—Preparation of 4-(4-ethynylpyridin-2-yl)morpholine

To a solution of 4-(4-((trimethylsilyl)ethynyl)pyridin-2-yl)morpholine (4.48 g, 17.2 mmol) in methanol (50 mL) was added potassium carbonate (4.76 g, 34.4 mmol). The reaction mixture was stirred at room temperature for 1 h at which time the methanol was removed via rotary evaporation. Water (35 mL) was added and the precipitate thus formed was collected via filtration to afford 4-(4-((trimethylsilyl)ethynyl)pyridin-2-yl)morpholine (1.85 g, 57% yield).

Step 4—Preparation of 3-((2-morpholinopyridin-4-yl)ethynyl)-5-nitropyridin-2-amine (Id)

A mixture of 3-bromo-5-nitropyridin-2-amine (1.59 g, 7.33 mmol), PdCl2(PPh3)2 (0.154 g, 0.22 mmol), X-Phos (2-dicyclohexylphosphino-2',4',6'-triisopropylbiphenyl) (0.174 g, 0.365 mmol) and Cs2CO3 (6.23 g, 19.17 mmol) in dry acetonitrile (35 mL) was purged with argon and stirred at room temperature for 30 min. 4-(4-Ethynylpyridin-2-yl)morpholine (1.379 g, 7.33 mmol) was added, and the mixture was stirred at 60° C. for 20 h. The mixture was cooled to room temperature, filtered, the filter cake was washed with 20 mL of cold acetonitrile and triturated with water (3×20 mL) until pH of the filtrate was ~7. The filter cake was dried to give crude 3-(2-(2-morpholinopyridin-4-yl)ethynyl)-5-nitropyridin-2-amine Id (1.263 g), which was used without further purification in the next step.

Step 5—Preparation of 2,2,2-trifluoro-N-(3-((2-morpholinopyridin-4-yl)ethynyl)-5-nitro-pyridin-2-yl)acetamide (2d)

To a solution of 3-((2-morpholinopyridin-4-yl)ethynyl)-5-nitropyridin-2-amine (Id, 1.02 g, 3.13 mmol) in a 1:1 mixture of acetonitrile:NMP (3:3 mL) was added TFAA (0.567 mL, 4.08 mmol) dropwise over 10 min, and the reaction mixture was stirred at room temperature for 1 h. The solution was concentrated to remove the acetonitrile, and then diluted with cold water (20 mL). The material was collected by filtration to give 2,2,2-trifluoro-N-(3-((2-morpholinopyridin-4-yl)ethynyl)-5-nitropyridin-2-yl)acetamide 2d (1.23 g, 94% yield). ESI-MS m/z calc. 421.1, found 422.5 (M+H)+.

Step 6—Preparation of 4-(4-(5-nitro-1H-pyrrolo[2,3-b]pyridin-2-yl)pyridin-2-yl)morpholine (3d)

A mixture of 2,2,2-trifluoro-N-(3-((2-morpholinopyridin-4-yl)ethynyl)-5-nitropyridin-2-yl)acetamide (2d, 1 g, 2.37 mmol) and CuI (90 mg, 0.48 mmol) in NMP (6 mL) was stirred at 95° C. for 4 h. The reaction mixture was poured into 10% NH4Cl aqueous solution (20 mL) and 28% NH4OH (6 mL) and the mixture was stirred at room temperature for 1 h. The solid thus formed was collected by filtration and washed with water and methanol to give a mixture of desired 4-(4-(5-nitro-1H-pyrrolo[2,3-b]pyridin-2-yl)pyridin-2-yl)morpholine and 3-((2-morpholinopyridin-4-yl)ethynyl)-5-nitropyridin-2-amine (634 mg) in 1:1 molar ratio by $^1$H NMR. ESI-MS m/z calc. 325.12, found 326.1 (M+H)+.

The mixture of 4-(4-(5-nitro-1H-pyrrolo[2,3-b]pyridin-2-yl)pyridin-2-yl)morpholine and 3-((2-morpholinopyridin-4-yl)ethynyl)-5-nitropyridin-2-amine (634 mg) was dissolved in NMP (8 mL) and cesium carbonate (1.5 g, 4.6 mmol) was added. The mixture was degassed and stirred under nitrogen for 16 h at 90° C. Water (40 ml) was added and the material was collected and washed with water and methanol to give pure 4-(4-(5-nitro-1H-pyrrolo[2,3-b]pyridin-2-yl)pyridin-2-yl)morpholine 3d (611 mg, 96% yield). ESI-MS m/z calc. 325.12, found 326.0 (M+H)+.

Step 7—Preparation of 2-(2-morpholinopyridin-4-yl)-1H-pyrrolo[2,3-b]pyridin-5-amine (4d)

To a solution of 4-(4-(5-nitro-1H-pyrrolo[2,3-b]pyridin-2-yl)pyridin-2-yl)morpholine (3d, 464 mg, 1.43 mmol) in a mixture of tetrahydrofuran (20 mL) and EtOH (20 mL) was added 5% Pd/C (150 mg) and the mixture was hydrogenated in a Parr shaker at 45 psig for 18 h. The Pd catalyst was filtered off and the reaction mixture was concentrated to remove all solvents. Diethyl ether (10 mL) was added and the solid thus formed was collected by filtration to give 2-(2-morpholino-pyridin-4-yl)-1H-pyrrolo[2,3-b]pyridin-5-amine 4d (402 mg, 95% yield). ESI-MS m/z calc. 296.15, found 296.4 (M+H)+.

Step 8—Preparation of 3,4-dimethyl-N-(2-(2-morpholinopyridin-4-yl)-1H-pyrrolo[2,3-b]pyridin-5-yl)-1H-pyrazole-5-carboxamide (5d)

A solution of give 2-(2-morpholinopyridin-4-yl)-1H-pyrrolo[2,3-b]pyridin-5-amine (4d, 0.38 g, 1.29 mmol), 3,4-dimethyl-1H-pyrazole-5-carboxylic acid (6, 0.2 g, 1.55 mmol) and diisopropylethyl-amine (0.8 mL, 4.56 mmol) in DMF (2 mL) was cooled in an ice-water bath. A solution of PyBOP (0.74 g, 1.42 mmol) in DMF (1 mL) was added dropwise and the reaction mixture was stirred at room temperature for 16 h. Acetone (30 mL) was added and the precipitate thus formed was collected by filtration. The solid was washed with EtOH and diethyl ether to give 3,4-dimethyl-N-(2-(2-morpholinopyridin-4-yl)-1H-pyrrolo[2,3-b]pyridin-5-yl)-1H-pyrazole-5-carboxamide 5d (235 mg, 43.7% yield). ESI-MS m/z calc. 417.19, found 418.2 (M+H)+.

Example 5

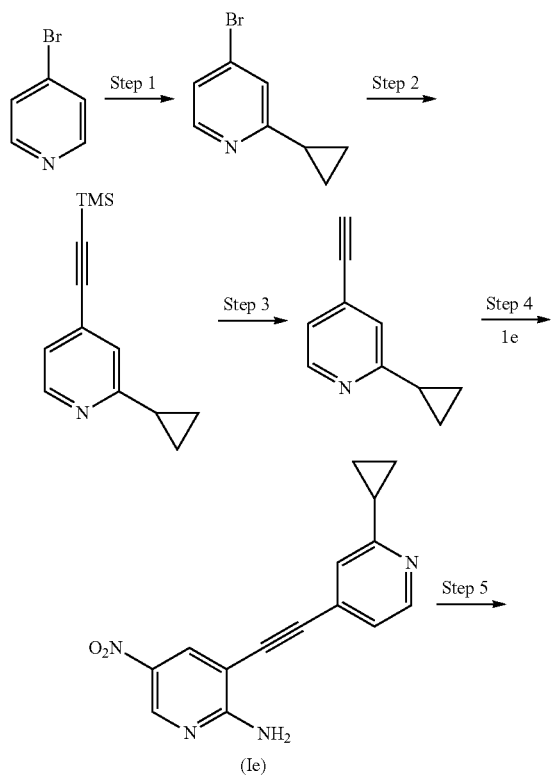

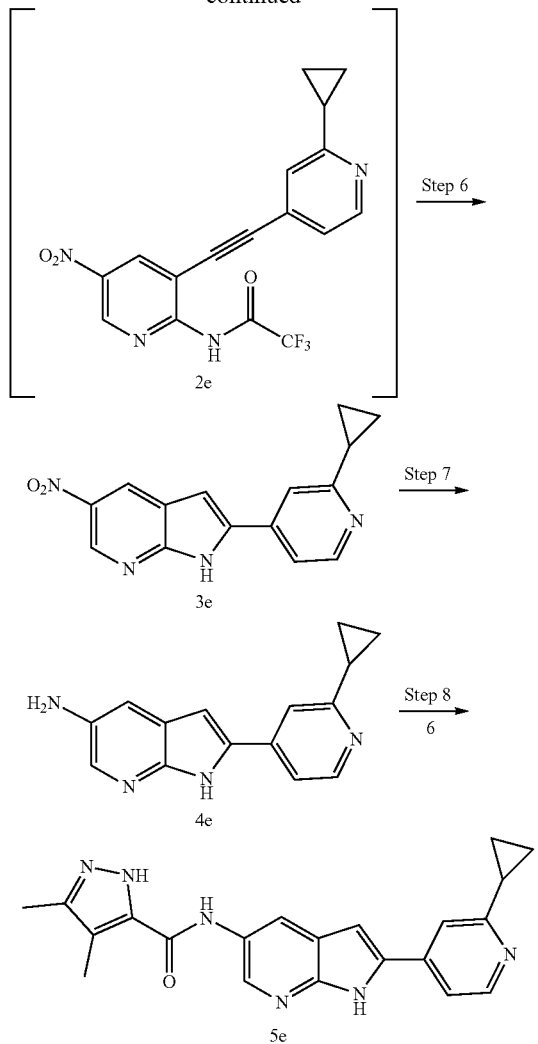

Step 1—Preparation of 4-bromo-2-cyclopropylpyridine

4-Bromopyridine hydrochloride (5.0 g, 43.27 mmol) was dissolved in THF (145 mL) and cooled to −78° C. To this solution cyclopropylmagnesium bromide solution in THF (135 mL, 0.7M, 95.19 mmol) was added dropwise. Then phenylchloroformate in hexane (5.5 mL, 1.25M, 43.27 mmol) was added to the solution. The reaction mixture was stirred at −78° C. for 10 minutes and allowed to warm to room temperature. The reaction was quenched by the addition of saturated NH$_4$Cl (aq) solution (50 mL). The layers were separated and the organic layer was washed with water (20 mL), 2M HCl (15 mL), water (20 mL), and brine (20 mL). The organic layer was dried over Na$_2$SO$_4$ and concentrated to give a brown oil. The brown oil was dissolved in toluene (180 mL) and DDQ (10.8 g, 47.60 mmol) was added. The reaction was allowed to stir overnight. After completion the reaction was quenched by the addition of 1M NaOH to pH~7, and the aqueous layer extracted three times with EtOAc (35 mL). The combined organic layers were washed with water and brine, then dried over Na$_2$SO$_4$ and concentrated to give 4-bromo-2-cyclopropylpyridine (3.6 g crude, 42% yield) which was used without further purification. ESI-MS m/z calc. 197.0 found 198.5 (M+H)⁺.

Step 2—Preparation of 2-cyclopropyl-4-((trimethylsilyl)ethynyl)pyridine

4-Bromo-2-cyclopropylpyridine (2.66 g, 13.5 mmol) was dissolved in THF (27 mL), and ethynyl-trimethylsilane (9.35 mL, 67.5 mmol), triethylamine (3.76 mL, 27 mmol), copper (I) iodide (28.6 mg, 0.675 mmol) and [1,1'-bis(diphenylphosphino)ferrocene]-dichloropalladium(II) (473.8 mg, 6.75 mmol) were added sequentially. The reaction was stirred overnight, and upon completion was diluted with water (15 mL) and extracted three times with EtOAc (15 mL). The combined organic layers were dried over $Na_2SO_4$ and concentrated to dryness. The crude residue was dry loaded onto silica gel and purified by silica gel column chromatography eluting with 0-30% hexanes:EtOAc to afford 2-cyclopropyl-4-((trimethylsilyl)ethynyl)pyridine (2.46 g, 84% yield). ESI-MS m/z calc. 215.1, found 216.5 (M+H)⁺.

Step 3—Preparation of 2-cyclopropyl-4-ethynylpyridine

2-Cyclopropyl-4-((trimethylsilyl)ethynyl)pyridine (2.46 g, 11.44 mmol) was dissolved in methanol (48 mL) and $K_2CO_3$ (3.16 g, 22.88 mmol) was added to the solution. After stirring for 30 min, the solids were filtered off, and the filtrate was dry loaded onto silica gel. The crude mixture was purified by silica gel column chromatography eluting with 0-30% hexanes:EtOAc to give 2-cyclopropyl-4-ethynylpyridine (550 mg, 34% yield). ESI-MS m/z calc. 143.1, found 144.2 (M+H)⁺.

Step 4—Preparation of 3-((2-cyclopropylpyridin-4-yl)ethynyl)-5-nitropyridin-2-amine (1e)

3-Bromo-5-nitropyridin-2-amine (1e) (450 mg, 2.06 mmol) was dissolved in MeCN (5 mL) and [1,1'-Bis-(diphenylphosphino)ferrocene]dichloropalladium(II) (14.5 mg, 0.02 mmol), copper (I) iodide (3.9 mg, 0.02 mmol), diisopropylamine (1.73 mL, 12.36 mmol) were added sequentially. The solution was degassed with N2 for 3 minutes and a solution of 2-cyclopropyl-4-ethynylpyridine (354 mg, 2.47 mmol) in acetonitrile (1 mL) was added slowly over an hour. The reaction was stirred overnight at 50° C., during which time a green precipitate formed. The precipitate was collected by filtration and washing the filter cake with methanol. This green solid was purified by reverse phase HPLC to give 3-((2-cyclopropyl-pyridin-4-yl)ethynyl)-5-nitropyridin-2-amine (58 mg, 10% yield). ESI-MS m/z calc. 280.1, found 281.4 (M+H)⁺.

Steps 5 and 6—Preparation of 2-(2-cyclopropylpyridin-4-yl)-5-nitro-1H-pyrrolo[2,3-b]pyridine (3e)

3-((2-Cyclopropylpyridin-4-yl)ethynyl)-5-nitropyridin-2-amine (58 mg, 0.21 mmol) was dissolved in NMP and $CS_2CO_3$ (135 mg, 0.42 mmol) was added to the solution. The mixture was stirred overnight at 90° C. The reaction mixture was diluted with water (5 mL), and centrifuged. The resulting pellet was washed with water (5 mL) and centrifuged again. The pellet was collected and dried to give 2-(2-cyclopropyl-pyridin-4-yl)-5-nitro-1H-pyrrolo[2,3-b]pyridine (36 mg, 62% yield). ESI-MS m/z calc. 280.1, found 281.3 (M+H)⁺.

Step 7—Preparation of 2-(2-cyclopropylpyridin-4-yl)-1H-pyrrolo[2,3-b]pyridin-5-amine (4e)

2-(2-Cyclopropylpyridin-4-yl)-5-nitro-1H-pyrrolo[2,3-b] pyridine (36 mg, 0.13 mmol) was dissolved in THF then added to 5% Pd/C (15 mg) in a Parr vessel. The reaction was shaken overnight on a Parr reactor under 45 psig of hydrogen gas. Upon completion the mixture was filtered through Celite and the filtrate concentrated to give 2-(2-cyclopropylpyridin-4-yl)-1H-pyrrolo[2,3-b]pyridin-5-amine (28.3 mg, 87% yield). ESI-MS m/z calc. 250.1, found 251.5 (M+H)⁺.

Step 8—Preparation of N-(2-(2-cyclopropylpyridin-4-yl)-1H-pyrrolo[2,3-b]pyridin-5-yl)-3,4-dimethyl-1H-pyrazole-5-carboxamide (Compound 5e)

2-(2-Cyclopropylpyridin-4-yl)-1H-pyrrolo[2,3-b]pyridin-5-amine (28.3 mg, 0.11 mmol) was dissolved in DMF (2 mL) and 3,4-dimethyl-1H-pyrazole-5-carboxylic acid (6) (17.4 mg, 0.12 mmol) and diisopropyl-ethylamine (0.024 mL, 0.13 mmol) were added. The solution was cooled to 0° C. in an ice bath and a solution of benzotriazol-1-yloxytripyrrolidinophosphonium hexafluorophosphate (PyBOP) (64.5 mg, 0.12 mmol) in DMF (1 mL) was added dropwise. After stirring overnight at room temperature, the crude reaction solution was submitted for reverse-phase HPLC purification to afford N-(2-(2-cyclopropylpyridin-4-yl)-1H-pyrrolo[2,3-b]pyridin-5-yl)-3,4-dimethyl-1H-pyrazole-5-carboxamide (33 mg, 79% yield). ESI-MS m/z calc. 372.2, found 373.4 (M+H)⁺.

All patents, patent applications and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

While this invention has been disclosed with reference to specific embodiments, it is apparent that other embodiments and variations of this invention may be devised by others skilled in the art without departing from the true spirit and scope of the invention.

Also, unless indicated to the contrary, where various numerical values are provided for embodiments, additional embodiments are described by taking any two different values as the endpoints of a range. Such ranges are also within the scope of the disclosure.

Thus, additional embodiments are within the scope of the disclosure and within the following claims.

What is claimed is:

1. A compound of Formula 2:

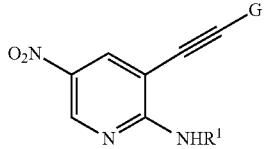

or a salt, a solvate, a tautomer, a stereoisomer or a deuterated analog thereof, wherein:
$R^1$ is $C(O)R^2$;
$R^2$ is alkyl optionally substituted with 1-5 halogens;
G is phenyl or a 5-6 membered heteroaryl optionally substituted with 1-2 $R^3$; and
each $R^3$ is independently $C_1$-$C_6$ alkyl, CN, $C_1$-$C_6$ alkyl-CN, 3-6 membered cycloalkyl, or 4-6 membered heterocycloalkyl.

2. A method for preparing a compound of Formula 2:

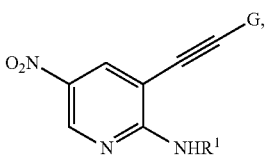

or a salt, a solvate, a tautomer, a stereoisomer or a deuterated analog thereof, said method comprising:
contacting a compound of Formula (I) or a salt thereof:

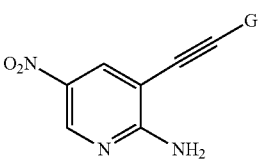

with an acetic anhydride, or a derivative thereof, to form the compound of Formula 2, wherein
$R^1$ is $C(O)R^2$;
$R^2$ is alkyl optionally substituted with 1-5 halogens;
G is phenyl or a 5-6 membered heteroaryl optionally substituted with 1-2 $R^3$; and
each $R^3$ is independently $C_1$-$C_6$ alkyl, CN, $C_1$-$C_6$ alkyl-CN, 3-6 membered cycloalkyl, or 4-6 membered heterocycloalkyl.

3. The method according to claim 2, wherein the acetic anhydride is trifluoroacetic anhydride.

4. A method for preparing a compound of Formula 3:

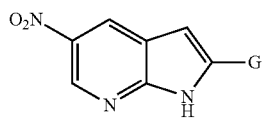

or a salt, a solvate, a tautomer, a stereoisomer or a deuterated analog thereof, comprising:
contacting a compound of Formula (I) or a salt thereof:

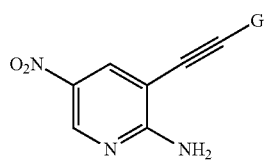

with an acetic anhydride, or a derivative thereof, to form the compound of Formula 2 according to claim 2; and
refluxing a compound of Formula 2 with an acetic anhydride, or a derivative thereof, in a suitable solvent to form a compound of Formula 3.

5. The method according to claim 4, wherein the acetic anhydride is trifluoroacetic anhydride.

6. The method according to claim 4, wherein the suitable solvent is acetonitrile.

7. A method for preparing a compound of Formula 4:

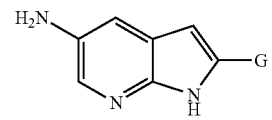

or a salt, a solvate, a tautomer, a stereoisomer or a deuterated analog thereof, comprising:
contacting a compound of Formula (I) or a salt thereof:

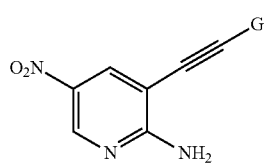

with an acetic anhydride, or a derivative thereof, to form the compound of Formula 2 according to claim 2;
refluxing a compound of Formula 2 with an acetic anhydride, or a derivative thereof, in a suitable solvent to form a compound of Formula 3 or a salt thereof

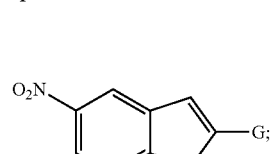

and
reducing a compound of Formula 3 to form a compound of Formula 4.

8. A method for preparing a compound of Formula 5:

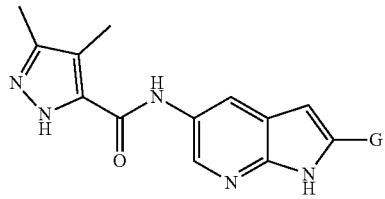

5 or a salt, a solvate, a tautomer, a stereoisomer or a deuterated analog thereof, comprising:

contacting a compound of Formula (I) or a salt thereof:

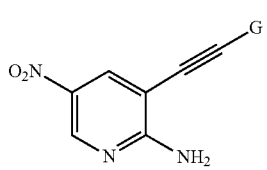

(I)

with an acetic anhydride, or a derivative thereof, to form the compound of Formula 2 according to claim 2;

refluxing a compound of Formula 2 with an acetic anhydride, or a derivative thereof, in a suitable solvent to form Formula 3 or a salt thereof

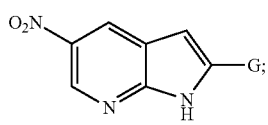

3 reducing a compound of Formula 3 to form a compound of Formula 4 or a salt thereof

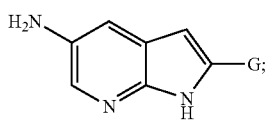

4 and
combining a compound of Formula 4 with a compound of Formula 6 or a salt thereof:

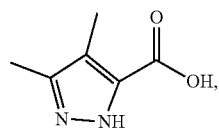

6 with a suitable coupling agent to form a compound of Formula 5.

9. The method according to claim 8, wherein the acetic anhydride is trifluoroacetic anhydride.

10. The method according to claim 8, wherein the suitable solvent is acetonitrile.

11. The method according to claim 8, wherein the suitable coupling agent is BOP, PyBOP, PyBrOP, TBTU, HBTU, HATU, COMU, or TFFH.

12. The method according to claim 11, wherein the suitable coupling agent is PyBOP.

13. A compound of Formula 2a:

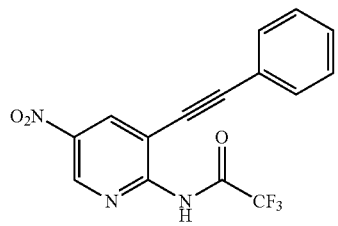

2a or a salt, a solvate, a tautomer, a stereoisomer or a deuterated analog thereof.

14. A compound of Formula 2e:

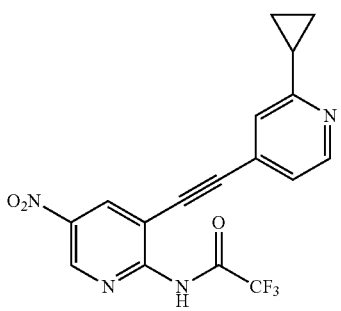

2e or a salt, a solvate, a tautomer, a stereoisomer or a deuterated analog thereof.

* * * * *